United States Patent
Zijl Van et al.

(10) Patent No.: US 12,264,129 B2
(45) Date of Patent: **\*Apr. 1, 2025**

(54) PROCESS FOR THE PREPARATION OF CHEMICAL PRODUCTS FROM WASTE PLASTIC FEEDSTOCKS

(71) Applicant: SABIC Global Technologies B.V., Bergen op Zoom (NL)

(72) Inventors: Anthoni Wouter Zijl Van, Eindhoven (NL); Nicolas Goyheneix, Riemst (BE); Lara Maria Galan-Sanchez, Eindhoven (NL); Christoph Roosen, Würselen (DE); Johan Pastwa, Elsloo (NL); Safa Farajzadeh Bibalan, Eindhoven (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/017,340

(22) PCT Filed: Jul. 15, 2021

(86) PCT No.: PCT/EP2021/069738
§ 371 (c)(1),
(2) Date: Jan. 20, 2023

(87) PCT Pub. No.: WO2022/017906
PCT Pub. Date: Jan. 27, 2022

(65) Prior Publication Data
US 2023/0295061 A1  Sep. 21, 2023

(30) Foreign Application Priority Data

Jul. 21, 2020  (EP) .................................. 20187003

(51) Int. Cl.
*C07C 4/04* (2006.01)
*C10B 53/07* (2006.01)

(52) U.S. Cl.
CPC ............... *C07C 4/04* (2013.01); *C10B 53/07* (2013.01)

(58) Field of Classification Search
CPC .................................. C07C 4/04; C10B 53/07
See application file for complete search history.

(56) References Cited

U.S. PATENT DOCUMENTS 10,513,661 B2 * 12/2019 Narayanaswamy .... C10B 47/24
2018/0002609 A1    1/2018 Narayanaswamy et al.
2019/0161683 A1    5/2019 Narayanaswamy et al.
2019/0299491 A1   10/2019 Stanislaus et al.
2020/0369966 A1   11/2020 Bitting et al.
2023/0257323 A1    8/2023 Zijl Van et al.
2023/0279179 A1    9/2023 Zijl Van et al.
2023/0287175 A1    9/2023 Zijl Van et al.
2023/0323213 A1   10/2023 Zijl Van et al.

FOREIGN PATENT DOCUMENTS

WO    2005110952 A1   11/2005
WO    2020152319 A1    7/2020
WO    2020242914 A1   12/2020

OTHER PUBLICATIONS

International Search Report for International Application No. PCT/EP2021/069738; International Filing Date Jul. 15, 2021; Date of Mailing Oct. 14, 2021; 4 pages.
Written Opinion for International Application No. PCT/EP2021/069738; International Filing Date Jul. 15, 2021; Date of Mailing Oct. 14, 2021; 6 pages.

* cited by examiner

*Primary Examiner* — Sharon Pregler
(74) *Attorney, Agent, or Firm* — CANTOR COLBURN LLP

(57) ABSTRACT

The present invention relates to a process for the production of butenes and butadienes from waste plastics feedstocks comprising the steps in this order of: (a) providing a hydrocarbon stream A obtained by treatment of a waste plastics feedstock; (b) providing a hydrocarbon stream B; (c) supplying a feed C comprising a fraction of the hydrocarbon stream A and a fraction of the hydrocarbon stream B to a thermal cracker furnace comprising cracking coil(s); (d) performing a thermal cracking operation in the presence of steam to obtain a cracked hydrocarbon stream D; (e) supplying the cracked hydrocarbon stream D to one or more separation units; (f) performing a separation operation to obtain different streams of chemical products comprising ethylene, propylene, isobutene, 1-butene, 2-butene, 1,2-butadiene, 1,3-butadiene, benzene, styrene, toluene, ethylbenzene and xylenes; wherein in step (d): • the coil outlet temperature is $\geq 800$ and $\leq 870°$ C., preferably $\geq 805$ and $\leq 835°$ C.; and • the weight ratio of steam to feed C is $>0.3$ and $<0.8$, preferably $>0.3$ and $<0.5$. Such process allows for optimisation of the quantity of waste plastic material that finds its way back into products that are produced as outcome of the process. The higher that quantity is, i.e. the higher the quantity of chemical building blocks that are present in the waste plastic material that are converted to the produced products, the better the sustainability footprint of the process is. The process allows for circular utilisation of plastics.

11 Claims, No Drawings

PROCESS FOR THE PREPARATION OF CHEMICAL PRODUCTS FROM WASTE PLASTIC FEEDSTOCKS

CROSS REFERENCE TO RELATED APPLICATIONS

This application is a National Stage application of PCT/EP2021/069738, filed Jul. 15, 2021, which claims the benefit of European Application No. 20187003.7, filed Jul. 21, 2020, both of which are incorporated by reference in their entireties herein.

The present invention relates to a process for the preparation of chemical products from products originating from waste plastic feedstocks. In particular, the invention relates to production of chemical products from products originating from waste plastic feedstocks with improved carbon efficiency towards such chemical products.

Presently, the disposal of plastic materials as a waste poses an increasing environmental issue. With increase of global population, and increase of use of plastic materials per capita, the quantity of plastic material that results as a waste, whether from industrial use or from consumer use, reaches such levels that far-reaching innovations in methods of disposal are rapidly becoming essential. In particular, it is very much desirable that such innovations also contribute to reduction of detrimental environmental issues, such as fossil carbon utilisation and carbon emissions into the atmosphere.

In many cases, at present, waste plastics are processed by incineration, leading to atmospheric carbon emissions, discarded in landfills, or even littered onto land and sea. Such undesired waste disposal increasingly faces societal objections. It is therefore an object of development in industry to find means of processing such waste plastics in a way overcoming the above objections.

One means of achieving such is via processing the waste plastics via chemical conversion processes into a feed material that again can find its way to the renewed production of plastics. Not only would such route allow for the re-use of a waste, with the problems associated to it as presented above, but also could it serve as a replacement of conventional feed materials that are used in the production of plastics.

A particular route for production of plastics, currently by and far the most widespread route, is via first processing of fossil oil or gas derivatives into building blocks for plastics, and further converting these building blocks into plastics via polymerisation processes. A typical example of such involves the preparation of such building blocks, also referred to as monomers, via steam cracking of fossil oil derivatives of the naphtha range. Such monomers include particularly lower mono- and diolefinic compounds, such as butenes and butadienes, next to other valuable chemical building blocks such as aromatics and oxygenated products. These chemical building blocks are on very large scale converted into polymer materials.

As chemical products that are obtained from steam cracking are used to a large extent in the production of plastics, this route would be particularly suitable for utilisation of waste plastics based feed streams to be converted into new polymeric materials. Such route would allow for providing a means to convert plastics to plastics, which is also referred to as circular plastics processing.

In order to be able to process waste plastics as a feed material for steam cracking operations, it has to be provided as a feed to the steam cracker in such way that the cracking process can be operated at the highest of efficiencies, and under sustainable conditions.

In this context, with high cracking efficiency it is meant that the cracking is performed under conditions leading to a maximised production of propylene and benzene as part of the product spectrum that is produced in the steam cracker. Steam cracking involves subjecting a feed stream of hydrocarbons of mixed chemical structure to a high temperature, under high flow velocities, for a certain time. As a result of these conditions, thermal degradation of the chemical compounds in the feed stream occurs, leading to a certain spectrum of desired chemical compounds that find their way into commercial use, either directly or via further chemical conversion processes.

By sustainable conditions of steam cracking in the context of the present invention is meant that the steam cracking occurs under such conditions of process and feed stream composition that the run duration of the cracking process, which in commercial operation is a continuous process, is as long as possible, before formation of coke or fouling due to contaminants and/or operational conditions that settles on the inside of the tubes which typically are employed in steam crackers as per the present art forces operations to be ceased and reactor tubes to be cleaned. This run duration is very much dependent on the composition of the feed material and the conditions of cracking, and is desirably as long as possible to enable an economic operation of the plant.

It is now an object of the present invention to provide a process that allows for the production of chemical products utilising a maximised efficiency of carbon originating from a waste plastics stream.

According to the present invention, this is now achieved by a process for the production of butenes and butadienes from waste plastics feedstocks comprising the steps in this order of:

(a) providing a hydrocarbon stream A obtained by treatment of a waste plastics feedstock;
(b) providing a hydrocarbon stream B;
(c) supplying a feed C comprising a fraction of the hydrocarbon stream A and a fraction of the hydrocarbon stream B to a thermal cracker furnace comprising cracking coil(s);
(d) performing a thermal cracking operation in the presence of steam to obtain a cracked hydrocarbon stream D;
(e) supplying the cracked hydrocarbon stream D to one or more separation units;
(f) performing a separation operation to obtain different streams of chemical products comprising ethylene, propylene, isobutene, 1-butene, 2-butene, 1,2-butadiene, 1,3-butadiene, benzene, styrene, toluene, ethylbenzene and xylenes;

wherein in step (d):
the coil outlet temperature is ≥800 and ≤870° C., preferably ≥805 and ≤835° C.; and
the weight ratio of steam to feed C is >0.3 and <0.8, preferably >0.3 and <0.5.

The process of the present invention allows for optimisation of the quantity of waste plastic material that finds its way back into a product that is produced as outcome of the process. The higher that quantity is, i.e. the higher the quantity of chemical building blocks that are present in the waste plastic material that are converted to the produced products, the better the sustainability footprint of the process is. The process allows for circular utilisation of plastics. In addition, the process allows for increased efficiency in the production of butenes and butadienes in that the fraction of thereof in the cracked hydrocarbon stream D is increased.

In the context of the present invention, chemical products are to be understood to be the group consisting of ethylene, propylene, 1-butene, isobutene, 2-butene, 1,2-butadiene, 1,3-butadiene, benzene, styrene, toluene, ethylbenzene and xylenes.

The weight ratio of steam to feed C may for example be >0.3 and <0.8, preferably >0.3 and <0.7, more preferably >0.30 and <0.50.

The process of the present invention allows for the conversion of the waste plastics material into chemical products.

The waste plastics feedstock that is used for the production of the hydrocarbon stream A of the present process may for example comprise polyolefins, polyesters, thermoplastic elastomers, polyvinyl chlorides, polystyrenes, or polycarbonates.

Waste plastic feedstocks that may be used for the production of the hydrocarbon stream A can be mixtures comprising polyolefins, polyesters, thermoplastic elastomers, polyvinyl chlorides, polystyrenes, or polycarbonates. In particular, the waste plastic feedstock that may be used for the production of the hydrocarbon stream A can be mixtures comprising >25.0 wt % of polyolefins, with regard to the total weight of the waste plastic feedstock. Preferably, the waste plastic feedstock may comprise >40.0 wt % of polyolefins, more preferably >50.0 wt %, even more preferably >60.0 wt %, or >70.0 wt %. The waste plastic feedstock may comprise a fraction of non-thermoplastics materials. Such non-thermoplastic materials may for example be hydrocarbon-based materials, such as rubber materials, but may also be materials including paper, sand and soil. It is an advantage of the present invention that waste plastics feedstocks containing at most 10 wt %, preferably at most 5.0 wt %, more preferably at most 2.0 wt %, of materials selected from paper, sand and soil, and combinations thereof, may be used in a process for preparation of polypropylene. This allows for the processing of such feedstocks without the need for cleaning processes that may require use of solvents or detergents.

For example, the waste plastics feedstock may comprise ≤10.0 wt % of ingredients being the sum of the content of glass, paper, metal, cardboard, compostable waste, wood, stone, textiles, rubber materials and superabsorbent hygiene products, with regard to the total weight of the waste plastics feedstock.

The waste plastics feedstock may for example comprise ≥90.0 wt % of polymeric material, with regard to the total weight of the waste plastics feedstock.

The waste plastics feedstock may for example comprise a quantity of polyesters. For example, the waste plastics feedstock may comprise <20.0 wt % of polyesters, preferably <15.0 wt %, more preferably <10.0 wt %, even more preferably <5.0 wt %, even further preferably <2.0 wt %. The waste plastics feedstock may in certain embodiments be free from polyesters.

A particular type of polyester that typically can be present in waste plastic feedstocks such as employed in the preparation of the hydrocarbon stream A as used in the present process is polyethylene terephthalate, which may also be referred to as PET. The waste plastics feedstock may for example comprise a quantity of PET. For example, the waste plastics feedstock may comprise <20.0 wt % of PET, preferably <15.0 wt %, more preferably <10.0 wt %, even more preferably <5.0 wt %, even further preferably <2.0 wt %. The waste plastics feedstock may in certain embodiments be free from PET.

Polyesters such as PET contain oxygen atoms in their polymeric chains. The presence of compounds comprising oxygen atoms in the hydrocarbon stream A is subject to certain limitation, since an excess quantity of oxygen atoms in the compounds that are supplied to the thermal cracker furnace may lead to problems including fouling and corrosion in the down-stream processing of the cracked hydrocarbon stream D exiting from the thermal cracker furnace. Accordingly, there is a desire to control or even minimise the quantity of oxygen-containing polymers in the waste plastics feedstock that is used to prepare the hydrocarbon stream A.

The waste plastics feedstock may for example comprise a quantity of polyamides. For example, the waste plastics feedstock may comprise <20.0 wt % of polyamides, preferably <15.0 wt %, more preferably <10.0 wt %, even more preferably <5.0 wt %, even further preferably <2.0 wt %. The waste plastics feedstock may in certain embodiments be free from polyamides.

Particular types of polyamide that typically can be present in waste plastic feedstocks such as employed in the preparation of the hydrocarbon stream A as used in the present process are polyamide 6 and polyamide 6,6, which may also be referred to as PA6 and PA66, respectively. The waste plastics feedstock may for example comprise a quantity of PA6 or PA66. For example, the waste plastics feedstock may comprise <20.0 wt % of total of PA 6 and PA66, preferably <15.0 wt %, more preferably <10.0 wt %, even more preferably <5.0 wt %, even further preferably <2.0 wt %. The waste plastics feedstock may in certain embodiments be free from PA6 and/or PA66.

The waste plastics feedstock may for example comprise a quantity of polyvinyl chlorides, which may also be referred to as PVC. For example, the waste plastics feedstock may comprise <5.0 wt % of PVC, preferably <2.0 wt %, more preferably <1.0 wt %, even more preferably <0.5 wt %, even further preferably <0.1 wt %. The waste plastics feedstock may in certain embodiments be free from PVC.

The waste plastics feedstock may for example comprise <20.0 wt %, preferably <10.0 wt % of polyesters; and/or <20.0 wt %, preferably <10.0 wt % of polyamides; and/or <2.0 wt %, preferably <1.0 wt % of polyvinyl chloride with regard to the total weight of polymeric material in the waste plastics feedstock.

The presented percentages of polyesters, polyamides and PVC in the waste plastics feedstock are to be understood to be percentages by weight of the total weight of polymeric material present in the waste plastics feedstock.

The waste plastic feedstock may further comprise a quantity of moisture, for example the waste plastics feedstock may contain up to 20.0 wt % of moisture, preferably up to 10.0 wt %, more preferably up to 5.0 wt %.

The present process allows for the cracked hydrocarbon stream D to contain a particularly high fraction of butenes and butadienes. The higher the fraction thereof in the cracked product, the better the efficiency of the process towards these product is.

It is preferred that the hydrocarbon stream A has an initial boiling point >25° C. and a final boiling point of <350° C., wherein the initial boiling point and the final boiling point are determined in accordance with ASTM D86 (2012).

The hydrocarbon stream A may for example have an initial boiling point of >25° C., preferably of >30° C., more preferably of >35° C., even more preferably of >40° C. The hydrocarbon stream A may for example have an initial boiling point of <100° C., preferably <90° C., more preferably <80° C., even more preferably <70° C., or <60° C., or <50° C.

The hydrocarbon stream A may for example have a final boiling point of <350° C., preferably of <325° C., more preferably of <300° C., even more preferably of <275° C., even more preferably of <250° C., or <225° C., or <200° C. The hydrocarbon stream A may for example have a final boiling point of >150° C., preferably >175° C., more preferably >200° C., even more preferably >250° C., or >275° C., or >300° C.

The hydrocarbon stream A is a material stream that is obtained by treatment of a waste plastics feedstock. For example, hydrocarbon stream A may be obtained by processing a waste plastics stream in a pyrolysis unit.

Such pyrolysis unit may be a continuously operating unit, wherein a stream of waste plastics is continuously supplied to the unit and at least a liquid stream comprising pyrolysis products is continuously obtained from the unit. Alternatively, the pyrolysis unit may be a batch-wise operating using wherein a quantity of waste plastics is introduced into the unit, subjected to pyrolysis conditions, and subsequently at least a liquid stream comprising pyrolysis products is obtained from the unit.

The pyrolysis process that is performed in the pyrolysis unit may be a low-severity pyrolysis process or a high-severity pyrolysis process. In a low-severity pyrolysis process, the pyrolysis may be performed at a temperature of ≥250° C. and ≤450° C., preferably ≥275° C. and ≤425° C., more preferably ≥300° C. and ≤400° C. Alternatively, the pyrolysis process may be a high-severity process performed at a temperature of ≥450° C. and ≤750° C., preferably ≥500° C. and ≤700° C., more preferably ≥550° C. and ≤650° C.

The pyrolysis process may be a catalytic process. In such pyrolysis process, for example a quantity of a zeolite catalyst such as a ZSM-5 zeolite catalyst may be used. In such pyrolysis process, for example a quantity of spent FCC catalyst may be used. In particular, a composition comprising a quantity of ZSM-5 catalyst and a quantity of spent FCC catalyst may be used. For example, a composition comprising a quantity of ZSM-5 and a quantity of spent FCC catalyst may be used, wherein the weight ratio of the spent FCC catalyst to the ZSM-5 catalyst is between 0.5 and 5.0, such as between 1.0 and 3.0.

From the pyrolysis process, a liquid hydrocarbon stream may be obtained. The liquid hydrocarbon stream may for example comprise a quantity of n-paraffins, a quantity of iso-paraffins, a quantity of olefins, a quantity of naphthenes, and/or a quantity of aromatics. The liquid hydrocarbon stream may for example comprise a quantity of n-paraffins, a quantity of iso-paraffins, a quantity of olefins, a quantity of naphthenes, and a quantity of aromatics.

In the context of the present invention, n-paraffins that may be present in the hydrocarbon stream A may for example include n-alkanes having 3 to 40 carbon atoms. The iso-paraffins that may be present in the hydrocarbon stream A may for example have 3 to 40 carbon atoms. The naphtenes that may be present in the hydrocarbon stream A may for example have 3 to 40 carbon atoms. The aromatics that may be present in the hydrocarbon stream A may for example have 6 to 40 carbon atoms.

The hydrocarbon stream A may for example comprise ≥25.0 and ≤95.0 wt % of n-paraffins, with regard to the total weight of the hydrocarbon stream A. Preferably, the hydrocarbon stream A comprises ≥25.0 and ≤80.0 wt % of n-paraffins, more preferably ≥25.0 and ≤70.0 wt %, even more preferably ≥25.0 and ≤50.0 wt %.

The hydrocarbon stream A may for example comprise ≥5.0 and ≤40.0 wt % of iso-paraffins, with regard to the total weight of the hydrocarbon stream A. Preferably, the hydrocarbon stream A comprises ≥5.0 and ≤30.0 wt % of iso-paraffins, more preferably ≥7.5 wt % and ≤25.0 wt %.

The hydrocarbon stream A may for example comprise ≤50.0 wt % of olefins, with regard to the total weight of the hydrocarbon stream A. Preferably, the hydrocarbon stream A comprises ≤40.0 wt % of olefins, more preferably ≤35.0 wt %, even more preferably ≤30.0 wt %.

The hydrocarbon stream A may for example comprise ≥5.0 and ≤50.0 wt % of olefins, with regard to the total weight of the hydrocarbon stream A. Preferably, the hydrocarbon stream A comprises ≥10.0 and ≤40.0 wt % of olefins, more preferably ≥15.0 and ≤35.0 wt %.

The hydrocarbon stream A may for example comprise ≥5.0 and ≤20.0 wt % of napthnenes, with regard to the total weight of the hydrocarbon stream A. Preferably, the hydrocarbon stream A comprises ≤5.0 and ≥15.0 wt % of naphthenes, more preferably ≥7.5 wt % and ≤15.0 wt %.

The hydrocarbon stream A may for example comprise ≤5.0 and ≥15.0 wt % of aromatics, with regard to the total weight of the hydrocarbon stream A. Preferably, the hydrocarbon stream A comprises ≤5.0 and ≥12.5 wt % of aromatics, more preferably ≥7.5 wt % and ≤12.5 wt %.

The hydrocarbon stream A may for example comprise:
≥25.0 and ≤95.0 wt %, preferably ≥25.0 and ≤70.0 wt %, more preferably ≤25.0 and ≤50.0 wt %, of n-paraffins; and/or
≥5.0 and ≤20.0 wt %, preferably ≥5.0 and ≤15.0 wt %, more preferably ≥7.5 and ≤15.0 wt %, of iso-paraffins; and/or
≥5.0 and ≤50.0 wt %, preferably ≥10.0 and ≤40.0 wt %, more preferably ≥15.0 and ≤35.0 wt %, of olefins; and/or
≥5.0 and ≤20.0 wt %, preferably ≥5.0 and ≤15.0 wt %, more preferably ≥7.5 and ≤15.0 wt %, of napthenes; and/or
≥5.0 and ≤15.0 wt %, preferably ≥5.0 and ≤12.5 wt %, more preferably ≥7.5 and ≤12.5 wt %, of aromatics
with regard to the total weight of the hydrocarbon stream A.

In the context of the present invention, the atomic chlorine content is to be understood to be the total weight of chlorine atoms present in molecules in the hydrocarbon stream as fraction of the total weight of the hydrocarbon stream. The atomic nitrogen content is to be understood to be the total weight of nitrogen atoms present in molecules in the hydrocarbon stream as fraction of the total weight of the hydrocarbon stream.

The hydrocarbon stream A may for example comprise a certain quantity of contaminants. For example, the hydrocarbon stream A may contain a quantity of compounds comprising chlorine atoms. The quantity of compounds comprising chlorine atoms may be expressed as the atomic chlorine content of the hydrocarbon stream A. For example, the hydrocarbon stream A may have an atomic chlorine content of <800 ppm by weight, as determined in accordance with ASTM UOP 779-08, preferably <700 ppm, more preferably <600 ppm, even more preferably <500 ppm, even more preferably <400 ppm.

The hydrocarbon stream A may comprise a quantity of compounds comprising nitrogen atoms. The quantity of compounds comprising nitrogen atoms may be expressed as the atomic nitrogen content of the hydrocarbon stream A. For example, the hydrocarbon stream A may have an atomic nitrogen content of <1600 ppm by weight, as determined in accordance with ASTM D5762 (2012), preferably <1500 ppm, more preferably <1400 ppm, even more preferably <1300 ppm, even more preferably <1200 ppm, or <1100 ppm, or <1000 ppm. For example, the hydrocarbon stream A may have an atomic nitrogen content of <100 ppm by weight as determined in accordance with ASTM D4629 (2017).

The hydrocarbon stream A may comprise a quantity of compounds containing olefinic unsaturations. An indication for the quantity of olefinic unsaturations is the bromine number of the hydrocarbon stream. The bromine number indicates the quantity of bromine in g that reacts with 100 g of the hydrocarbon specimen when tested under the conditions of ASTM D1159-07 (2012). For example, the hydrocarbon stream A as used in the process of the present invention may have a bromine number of <100, preferably <95, more preferably <90, even more preferably <85.

It is preferred that the hydrocarbon stream B has an initial boiling point >25° C. and a final boiling point of <350° C., wherein the initial boiling point and the final boiling point are determined in accordance with ASTM D86 (2012).

The hydrocarbon stream B may for example have an initial boiling point of >25° C., preferably of >30° C., more preferably of >35° C., even more preferably of >40° C. The hydrocarbon stream B may for example have an initial boiling point of <100° C., preferably <90° C., more preferably <80° C., even more preferably <70° C., or <60° C., or <50° C.

The hydrocarbon stream B may for example have a final boiling point of <350° C., preferably of <325° C., more preferably of <300° C., even more preferably of <275° C., even more preferably of <250° C., or <225° C., or <200° C. The hydrocarbon stream B may for example have a final boiling point of >150° C., preferably >175° C., more preferably >200° C., even more preferably >250° C., or >275° C., or >300° C.

The hydrocarbon stream B may for example comprise ≥25.0 and ≤95.0 wt % of n-paraffins, with regard to the total weight of the hydrocarbon stream B. Preferably, the stream A comprises ≥25.0 and ≤80.0 wt % of n-paraffins, more preferably ≥25.0 and ≥50.0 wt %.

The hydrocarbon stream B may for example comprise ≥5.0 and ≤40.0 wt % of iso-paraffins, with regard to the total weight of the hydrocarbon stream B. Preferably, the hydrocarbon stream B comprises ≥5.0 and ≤30.0 wt % of iso-paraffins, more preferably ≥7.5 wt % and ≤25.0 wt %.

The hydrocarbon stream B may for example comprise ≤2.0 wt % of olefins, with regard to the total weight of the hydrocarbon stream B. Preferably, the hydrocarbon stream B comprises ≤1.5 wt % of olefins, more preferably ≤1.0 wt %, even more preferably ≤0.5 wt %.

The hydrocarbon stream B may for example comprise ≥0.01 and ≤2.0 wt % of olefins, with regard to the total weight of the hydrocarbon stream B. Preferably, the hydrocarbon stream B comprises ≥0.01 and ≤1.5 wt % of olefins, more preferably ≥0.01 and ≤1.0 wt %.

The hydrocarbon stream B may for example comprise ≥0.5 and ≤50.0 wt % of napththenes, with regard to the total weight of the hydrocarbon stream B. Preferably, the hydrocarbon stream B comprises ≥5.0 and ≤40.0 wt % of naphthenes, more preferably ≥7.5 wt % and ≤30.0 wt %.

The hydrocarbon stream B may for example comprise ≥0.5 and ≤50.0 wt % of aromatics, with regard to the total weight of the hydrocarbon stream B. Preferably, the hydrocarbon stream B comprises ≥5.0 and ≤25.0 wt % of aromatics, more preferably ≥7.5 wt % and ≤20.0 wt %.

The hydrocarbon stream B may for example comprise:

≥25.0 and ≤95.0 wt %, preferably ≥25.0 and ≤80.0 wt %, more preferably ≥25.0 and ≤50.0 wt %, of n-paraffins; and/or ≥5.0 and ≤40.0 wt %, preferably ≥5.0 and ≤30.0 wt %, more preferably ≥7.5 and ≤25.0 wt %, of iso-paraffins; and/or ≤2.0 wt %, preferably ≥0.01 and ≤1.5 wt %, more preferably ≥0.01 and ≤1.0 wt %, of olefins; and/or ≥0.5 and ≤50.0 wt %, preferably ≥5.0 and ≤40.0 wt %, more preferably ≥7.5 and ≤30.0 wt %, of napthenes; and/or ≥0.5 and ≤50.0 wt %, preferably ≥5.0 and ≤25.0 wt %, more preferably ≥7.5 and ≤20.0 wt %, of aromatics with regard to the total weight of the hydrocarbon stream B.

The fraction of olefins $F_{O,C}$ in the feed C may be calculated as:

$$F_{O,C} = F_{O,A} * F_{A,C} + F_{O,B} * F_{B,C}$$

Wherein:
$F_{O,C}$ is the weight fraction of olefins in feed C, in wt %, with regard to the total weight of feed C;
$F_{O,A}$ is the weight fraction of olefins in the hydrocarbon stream A, in wt %, with regard to the total weight of hydrocarbon stream A;
$F_{O,B}$ is the weight fraction of olefins in the hydrocarbon stream B, in wt %, with regard to the total weight of hydrocarbon stream B;
$F_{A,C}$ is the weight fraction of hydrocarbon stream A in feed C, with regard to the total weight of feed C; and
$F_{B,C}$ is the weight fraction of hydrocarbon stream B in feed C, with regard to the total weight of feed C.

It is preferred that the fraction of olefins $F_{O,C}$ in the feed C is ≤2.0, preferably ≤1.8, more preferably ≤1.6, even more preferably ≤1.5 wt % with regard to the total weight of feed C.

The feed C that is supplied to the thermal cracker furnace comprises a fraction of the hydrocarbon stream A and a fraction of the hydrocarbon stream B.

The feed C may be supplied to the thermal cracker furnace via one or more inlet(s) wherein the fraction of the hydrocarbon stream A and the hydrocarbon stream B are combined prior to entering the thermal cracking furnace. Alternatively, the feed C may be supplied to the thermal cracking furnace in such way that the fraction of hydrocarbon stream A and the fraction of the hydrocarbon stream B enter the furnace via separate inlets.

The feed C may for example be a pre-mixed composition comprising a fraction of hydrocarbon stream A and a fraction of hydrocarbon stream B, wherein the feed C is supplied to the thermal cracking furnace as a mix via one or more inlets, or alternatively may be the total quantity of hydrocarbon stream A and hydrocarbon stream B, wherein the feed C is supplied to the thermal cracking furnace as separate streams of A and B, via one or more inlet(s) for each stream.

In the process of the present invention, the coil outlet temperature (COT) of the steam cracker furnace is ≥800 and ≤870° C., preferably ≥805 and ≤850° C., more preferably ≥805 and ≤835° C. Operating the cracker furnace in this temperature range of COT allows for cracking the feedstock to a desired product slate with maximized quantities of the desired chemical products, whilst ensuring a sustainable and durable operation of the cracker furnace.

The feed C may for example comprise a quantity of ≤90.0 wt % of hydrocarbon stream A, with regard to the total weight of feed C, for example ≤75.0 wt %, for example ≤60.0 wt %, for example ≤50.0 wt %, for example ≤40.0 wt %, for example ≤25.0 wt %, for example ≤20.0 wt %, for example ≤10.0 wt %. The feed C may for example comprise a quantity of ≥1.0 and ≤90.0 wt % of hydrocarbon stream A, with regard to the total weight of feed C, for example ≥1.0 and ≤75.0 wt %, for example ≥1.0 and ≤60.0 wt %, for example ≥1.0 and ≤50.0 wt %, for example ≥1.0 and ≤40.0 wt %, for example ≥1.0 and ≤25.0 wt %, for example ≥1.0 and ≤20.0 wt %, for example ≥1.0 and ≤10.0 wt %.

The feed C may for example comprise ≤10.0 wt %, preferably ≤5.0 wt %, more preferably ≥0.1 and ≤5.0 wt %, of hydrocarbon stream A, with regard to the total weight of feed C, preferably wherein hydrocarbon stream A is obtain as liquid stream from a pyrolysis unit.

In the process according to the present invention, the thermal cracking step (d) may be performed by utilising a feed C that comprises a minor fraction of hydrocarbon stream A. For example, the feed C that is supplied to the thermal cracking furnace may comprise a quantity of ≤5.0 wt % of hydrocarbon stream A, with regard to the total weight of feed C. For example, the feed C may comprise >95.0 wt % of hydrocarbon stream B, with regard to the total weight of feed C.

Such operation of the process of the invention presents as benefit that is allows for the use of a hydrocarbon stream A that is directly obtained as liquid stream from a pyrolysis unit without the need for further treatment of that liquid stream prior to supplying it to the thermal cracker furnace. This would allow the conversion of waste plastics as a certain fraction of a feed for a thermal cracking furnace without the need for subjecting the liquid product of the pyrolysis unit to a treatment step, and thereby contributes to process economics of the conversion of waste plastics to new chemical products.

For example, the feed C may comprise ≤5.0 wt %, preferably ≤4.0 wt %, more preferably ≤3.0 wt %, even more preferably ≤2.0 wt %, of hydrocarbon stream A, preferably wherein hydrocarbon stream A is obtained as liquid stream from a pyrolysis unit. In such embodiment, the hydrocarbon stream A may have:
- an atomic chlorine content of <600 ppm by weight as determined in accordance with ASTM UOP 779-08; and/or
- an atomic nitrogen content of <1600 ppm by weight as determined in accordance with ASTM D5762 (2012); and/or
- a bromine number of <100 as determined in accordance with ASTM D1159-07 (2012).

For example, the feed C may comprise ≥0.1 and ≤5.0 wt %, preferably ≥0.1 and ≤4.0 wt %, more preferably ≥0.1 and ≤3.0 wt %, even more preferably ≥0.1 and ≤2.0 wt %, of hydrocarbon stream A, preferably wherein hydrocarbon stream A is obtain as liquid stream from a pyrolysis unit. In such embodiment, the hydrocarbon stream A may have:
- an atomic chlorine content of <600 ppm by weight as determined in accordance with ASTM UOP 779-08; and/or
- an atomic nitrogen content of <1600 ppm by weight as determined in accordance with ASTM D5762 (2012); and/or
- a bromine number of <100 as determined in accordance with ASTM D1159-07 (2012).

For example, the feed C may consist of a fraction of the hydrocarbon stream B and ≥0.1 and ≤5.0 wt %, preferably ≥0.1 and ≤4.0 wt %, more preferably ≥0.1 and ≤3.0 wt %, even more preferably ≥0.1 and ≤2.0 wt %, of hydrocarbon stream A, preferably wherein hydrocarbon stream A is obtain as liquid stream from a pyrolysis unit.

After the thermal cracking operation (d) is performed, a cracked hydrocarbon stream D is obtained from the thermal cracking furnace. The composition of the cracked hydrocarbon stream D depends on the composition of the feed stream C. Typically, a cracked hydrocarbon stream comprises mono-olefins such as ethylene, propylene, butylenes, di-olefins such as butadiene, and aromatic compounds. In view of optimised process utilisation, it is desired that the quantity of ethylene and propylene in the cracked hydrocarbon stream D is high. The cracked hydrocarbon stream D may for example comprise ≥40.0 wt % of the total of ethylene and propylene, with regard to the total weight of the stream D. Preferably, the stream D may comprise ≥45.0 wt % of the total of ethylene and propylene, more preferably ≥50.0 wt % of the total of ethylene and propylene.

The process of the present invention allows for production of a particularly high quantity of chemical products as part of the cracked hydrocarbon stream D. For example, the quantity of butenes and butadienes in the stream D may be ≥8.0 wt %. For example, the quantity of ethylene in the stream D may be ≥24.0 wt %, preferably ≥25.0 wt %. For example, the quantity of propylene in the stream D may be ≥13.0 wt %, more preferably ≥14.0 wt %. For example, the quantity of aromatics in the stream D may be ≥20.0 wt %, preferably ≥21.0 wt %. For example, the quantity of valuable chemicals in the stream D may be ≥65.0 wt %.

Upon exiting the thermal cracking furnace, the cracked hydrocarbon stream D is supplied to a separation unit. In the separation unit, a separation operation is performed to obtain different streams comprising ethylene, propylene, isobutene, 1-butene, 2-butene, 1,2-butadiene, 1,3-butadiene, benzene, styrene, toluene, ethylbenzene and xylenes.

The invention will now be illustrated by the following non-limiting examples. The presented values for the examples have been obtained by modelling steam cracking operations of various feedstocks using as modelling software the Spyro 6.5 package, a commercially available modelling software package obtainable from Technip/Pyrotec.

Modelling was performed using feedstocks having the compositions as set out below in table 1.

TABLE 1

Compositions of feedstocks used in modelling via Spyro 6.5.

|  | FF | PY |
|---|---|---|
| n-paraffins | 30 | 43 |
| iso-paraffins | 32 | 17 |
| olefins | 0 | 19 |
| napthenes | 19 | 10 |
| aromatics | 19 | 11 |

Wherein the percentage as expressed represents a weight percentage of the respective fractions with regard to the total weight of the feedstock.

FF is a conventional fossil feedstock of the naphtha range and corresponds to hydrocarbon stream B as defined in the current invention. PY is a feed obtained as liquid stream from the pyrolysis of waste plastics and corresponds to hydrocarbon stream A as defined in the current invention.

Using the above feedstocks, a number of calculations using the Spyro 6.5 package were performed according to the conditions set out below in table 2.

TABLE 2

Conditions for modelling in Spyro 6.5.

| Experiment | Feed | COT | S/O |
|---|---|---|---|
| 1A | 100% FF | 810 | 0.35 |
| 1B | 5.0% PY; 95.0% FF | 810 | 0.35 |
| 1C | 10.0% PY; 90.0% FF | 810 | 0.35 |
| 2A | 100% FF | 820 | 0.35 |
| 2B | 5.0% PY; 95.0% FF | 820 | 0.35 |
| 2C | 10.0% PY; 90.0% FF | 820 | 0.35 |
| 3A | 100% FF | 840 | 0.35 |
| 3B | 5.0% PY; 95.0% FF | 840 | 0.35 |
| 3C | 10.0% PY; 90.0% FF | 840 | 0.35 |
| 4A | 100% FF | 860 | 0.35 |
| 4B | 5.0% PY; 95.0% FF | 860 | 0.35 |
| 4C | 10.0% PY; 90.0% FF | 860 | 0.35 |

Wherein:
Feed is the composition of feed C, wherein the percentages are in wt % of each of the feedstocks with regard to the total weight of feed C.
COT is the coil outlet temperature of the steam cracker furnace, in ° C.
S/O is the weight ratio of steam to feed C.
Using the above conditions, the model calculations provided the product slate of the cracking operations performed for each of the listed experiments, results of which are presented below.

| Experiment | Total | C2= | C3= | Ar | C4 |
|---|---|---|---|---|---|
| 1A | 65.69 | 23.13 | 14.14 | 19.56 | 8.87 |
| 1B | 65.66 | 23.30 | 14.18 | 19.30 | 8.88 |
| 1C | 65.63 | 23.48 | 14.22 | 19.03 | 8.90 |
| 2A | 65.87 | 23.89 | 13.60 | 20.07 | 8.32 |
| 2B | 65.84 | 24.06 | 13.64 | 19.81 | 8.33 |
| 2C | 65.82 | 24.22 | 13.68 | 19.57 | 8.35 |
| 3A | 65.48 | 25.24 | 12.17 | 20.93 | 7.13 |
| 3B | 65.45 | 25.40 | 12.21 | 20.70 | 7.14 |
| 3C | 65.43 | 25.56 | 12.24 | 20.48 | 7.15 |
| 4A | 64.17 | 26.39 | 10.34 | 21.53 | 5.90 |
| 4B | 64.15 | 26.54 | 10.37 | 21.32 | 5.91 |
| 4C | 64.14 | 26.69 | 10.40 | 21.12 | 5.93 |

Wherein:
C2= is the wt % of ethylene as part of the cracked hydrocarbon stream, corresponding to the cracked hydrocarbon stream D as defined in the present invention.
C3= is the wt % of propylene as part of the cracked hydrocarbon stream, corresponding to the cracked hydrocarbon stream D as defined in the present invention.
Ar is the total wt % of benzene, styrene, toluene, ethylbenzene and xylenes as part of the cracked hydrocarbon stream, corresponding to the cracked hydrocarbon stream D as defined in the present invention.
C4 is the total wt % of isobutene, 1-butene, 2-butene, 1,2-butadiene and 1,3-butadiene as part of the cracked hydrocarbon stream, corresponding to the cracked hydrocarbon stream D as defined in the present invention.
Total is the total wt % of C2=, C3=, Ar and C4 as part of the cracked hydrocarbon stream, corresponding to the cracked hydrocarbon stream D as defined in the present invention.

As indicated by the results of the cracker modelling above, the process according to the present invention allows for the optimization of yield of valuable chemical products, whilst allowing for a circular use of waste plastics given the feedstock being based on waste plastics.

The invention claimed is:

1. Process for the production of butenes and butadienes from waste plastics feedstocks comprising the steps in this order of:
    (a) providing a hydrocarbon stream A obtained by treatment of a waste plastics feedstock;
    (b) providing a hydrocarbon stream B;
    (c) supplying a feed C comprising a fraction of the hydrocarbon stream A and a fraction of the hydrocarbon stream B to a thermal cracker furnace comprising cracking coil(s);
    (d) performing a thermal cracking operation in the presence of steam to obtain a cracked hydrocarbon stream D;
    (e) supplying the cracked hydrocarbon stream D to one or more separation units;
    (f) performing a separation operation to obtain different streams of chemical products comprising ethylene, propylene, isobutene, 1-butene, 2-butene, 1,2-butadiene, 1,3-butadiene, benzene, styrene, toluene, ethylbenzene and xylenes;
    wherein in step (d):
        the coil outlet temperature is ≥800 and ≤870° C.; and
        the weight ratio of steam to feed C is >0.3 and <0.5,
    wherein
        the hydrocarbon stream A comprises:
            ≥25.0 and ≤50.0 wt % of n-paraffins; and
            ≥5.0 and ≤20.0 wt % of iso-paraffins; and
            ≥5.0 and ≤50.0 wt % of olefins; and
            ≥5.0 and ≤20.0 wt % of napthenes; and
            ≥5.0 and ≤15.0 wt % of aromatics;
        with regard to the total weight of the hydrocarbon stream A.

2. Process according to claim 1, wherein the hydrocarbon stream A has an initial boiling point >25° C. and a final boiling point of <350° C., wherein the initial boiling point and the final boiling point are determined in accordance with ASTM D86 (2012).

3. Process according to claim 1, wherein the hydrocarbon stream A has an atomic chlorine content of <800 ppm by weight as determined in accordance with ASTM UOP 779-08.

4. Process according to claim 1, wherein the hydrocarbon stream A has an atomic nitrogen content of <1600 ppm by weight as determined in accordance with ASTM D5762 (2012).

5. Process according to claim 1, wherein the hydrocarbon stream A has a bromine number of <100 as determined in accordance with ASTM D1159-07 (2012).

6. Process according to claim 1, wherein
    (i) the hydrocarbon stream A comprises:
        ≥5.0 and ≤15.0 wt % of iso-paraffins; and/or
        ≥10.0 and ≤40.0 wt % of olefins; and/or
        ≥5.0 and ≤15.0 wt % of napthenes; and/or
        ≥5.0 and ≤12.5 wt % of aromatics;
        with regard to the total weight of the hydrocarbon stream A; and/or
    (ii) the hydrocarbon stream B comprises:
        ≥25.0 and ≤95.0 wt % of n-paraffins; and/or
        ≥5.0 and ≤40.0 wt % of iso-paraffins; and/or
        ≤2.0 wt % of olefins; and/or
        ≥0.5 and ≤50.0 wt % of napthenes; and/or
        ≥0.5 and ≤50.0 wt % of aromatics
        with regard to the total weight of the hydrocarbon stream B.

7. Process according to claim 1, wherein in step (c), the feed C comprises≤10.0 wt % of hydrocarbon stream A, with regard to the total weight of feed C.

8. Process according to claim 1, wherein the treatment of the waste plastics feedstock to obtain hydrocarbon stream A involves a pyrolysis treatment.

9. Process according to claim 1, wherein the waste plastics feedstock comprises ≥90.0 wt % of polymeric material, with regard to the total weight of the waste plastics feedstock.

10. Process according to claim 1, wherein the waste plastics feedstock comprises
    <20.0 wt % of polyesters; and/or
    <20.0 wt % of polyamides; and/or
    <2.0 wt % of polyvinyl chloride
    with regard to the total weight of polymeric material in the waste plastics feedstock.

11. Process according to claim 1, wherein the waste plastics feedstock comprises≤10.0 wt % of ingredients being the sum of the content of glass, paper, metal, cardboard, compostable waste, wood, stone, textiles, rubber materials and superabsorbent hygiene products, with regard to the total weight of the waste plastics feedstock.

\* \* \* \* \*